(12) United States Patent
Zhou et al.

(10) Patent No.: US 6,559,620 B2
(45) Date of Patent: May 6, 2003

(54) SYSTEM AND METHOD FOR REMOTE MONITORING UTILIZING A RECHARGEABLE BATTERY

(75) Inventors: Peter Y. Zhou, Smithtown, NY (US); Dexing Pang, Smithtown, NY (US)

(73) Assignee: Digital Angel Corporation, So. St. Paul, MN (US)

( * ) Notice: Subject to any disclaimer, the term of this patent is extended or adjusted under 35 U.S.C. 154(b) by 0 days.

(21) Appl. No.: 09/813,477

(22) Filed: Mar. 21, 2001

(65) Prior Publication Data

US 2002/0135336 A1 Sep. 26, 2002

(51) Int. Cl.⁷ .................. H01M 10/46; H01M 10/44
(52) U.S. Cl. ............................................. 320/101
(58) Field of Search ................................. 320/101, 103, 320/104, 123, 132, 135, 137, 136, 150; 323/906; 136/291, 293

(56) References Cited

U.S. PATENT DOCUMENTS

| | | |
|---|---|---|
| 4,163,447 A | 8/1979 | Orr |
| 4,468,656 A | 8/1984 | Clifford et al. |
| 4,531,526 A | 7/1985 | Genest |
| 4,619,653 A | 10/1986 | Fischell |
| 4,665,385 A | 5/1987 | Henderson |
| 4,706,689 A | 11/1987 | Man |
| 5,043,736 A | 8/1991 | Darnell et al. |
| 5,119,102 A | 6/1992 | Barnard |
| 5,153,584 A | 10/1992 | Engira |
| 5,204,670 A | 4/1993 | Stinton |
| 5,235,633 A | 8/1993 | Dennison et al. |
| 5,299,132 A | 3/1994 | Wortham |
| 5,379,224 A | 1/1995 | Brown et al. |
| 5,389,934 A | 2/1995 | Kass |
| 5,418,537 A | 5/1995 | Bird |
| 5,461,365 A | 10/1995 | Schlager et al. |
| 5,462,051 A | 10/1995 | Oka et al. |
| 5,519,403 A | 5/1996 | Bickley et al. |
| 5,519,760 A | 5/1996 | Borkowski et al. |
| 5,552,772 A | 9/1996 | Janky et al. |
| 5,565,858 A | 10/1996 | Guthrie |
| 5,594,425 A | 1/1997 | Ladner et al. |
| 5,624,376 A | 4/1997 | Ball et al. |
| 5,626,630 A | 5/1997 | Markowitz et al. |
| 5,629,678 A | 5/1997 | Gargano et al. |
| 5,630,206 A | 5/1997 | Urban et al. |
| 5,650,770 A | 7/1997 | Schlager et al. |
| 5,652,570 A | 7/1997 | Lepkofker |
| 5,712,619 A | 1/1998 | Simkin |
| 5,714,931 A | 2/1998 | Petite et al. |
| 5,724,025 A | 3/1998 | Tavori |
| 5,742,233 A | 4/1998 | Hoffman et al. |
| 5,742,509 A | 4/1998 | Goldberg et al. |
| 5,748,147 A | 5/1998 | Bickley et al. |
| 5,749,909 A * | 5/1998 | Schroeppel et al. |
| 5,751,246 A | 5/1998 | Hertel |
| 5,767,788 A | 6/1998 | Ness |
| 5,772,586 A | 6/1998 | Heinonen et al. |
| 5,791,294 A | 8/1998 | Manning |
| 5,838,237 A | 11/1998 | Revell et al. |
| 5,874,897 A | 2/1999 | Klempau et al. |
| 5,892,454 A | 4/1999 | Schipper et al. |
| 5,905,450 A | 5/1999 | Kim et al. |
| 5,917,425 A | 6/1999 | Crimmins et al. |
| 5,939,982 A | 8/1999 | Gagnon et al. |
| 5,963,130 A | 10/1999 | Schlager et al. |
| 5,971,931 A | 10/1999 | Raff |
| 5,977,913 A | 11/1999 | Christ |
| 5,982,281 A | 11/1999 | Layson, Jr. |
| 6,026,304 A | 2/2000 | Hilsenrath et al. |
| 6,028,514 A | 2/2000 | Lemelson et al. |
| 6,031,454 A | 2/2000 | Lovejoy et al. |
| 6,034,622 A | 3/2000 | Levine |
| 6,046,687 A | 4/2000 | Janky |
| 6,069,570 A | 5/2000 | Herring |
| 6,072,396 A | 6/2000 | Gaukel |
| 6,078,804 A | 6/2000 | Alperovich et al. |
| 6,084,512 A | 7/2000 | Elberty et al. |
| 6,121,881 A | 9/2000 | Bieback et al. |
| 6,127,925 A | 10/2000 | Bonsignore et al. |
| 6,131,067 A | 10/2000 | Girerd et al. |
| 6,140,956 A | 10/2000 | Hillman et al. |
| 6,140,957 A | 10/2000 | Wilson et al. |
| 6,148,261 A | 11/2000 | Obradovich et al. |
| 6,154,676 A | 11/2000 | Levine |
| 6,157,841 A | 12/2000 | Bolduc et al. |
| 6,160,478 A | 12/2000 | Jacobsen et al. |
| 6,160,481 A | 12/2000 | Taylor, Jr. |
| 6,166,642 A | 12/2000 | Farshid |
| 6,167,276 A | 12/2000 | Pite |
| 6,169,484 B1 | 1/2001 | Schuchman et al. |
| 6,172,640 B1 * | 1/2001 | Durst et al. |
| 6,175,308 B1 | 1/2001 | Tallman et al. |
| 6,198,394 B1 | 3/2001 | Jacobsen et al. |
| 6,198,930 B1 | 3/2001 | Schipper |
| 6,199,550 B1 | 3/2001 | Wiesmann et al. |
| 6,208,290 B1 | 3/2001 | Krasner |
| 6,211,781 B1 | 4/2001 | McDonald |
| 6,219,556 B1 | 4/2001 | Lee |
| 6,225,901 B1 | 5/2001 | Kail, IV |
| 6,236,358 B1 | 5/2001 | Durst et al. |
| 6,300,903 B1 | 10/2001 | Richards et al. |
| 6,313,791 B1 | 11/2001 | Klanke |
| 6,421,001 B1 | 7/2002 | Durst et al. |

* cited by examiner

Primary Examiner—Edward H. Tso
(74) Attorney, Agent, or Firm—Stroock & Stroock & Lavan LLP

(57) ABSTRACT

A method and a system for remotely monitoring a person includes a portable unit including a self-recharging battery, the portable unit being adapted to monitor a biological parameter and a physical location of the person; a global positioning satellite transmitting global positioning system (GPS) data to the portable unit; and a central unit disposed remotely from the portable unit, the central unit being in communication with the portable unit via a ground station.

26 Claims, 4 Drawing Sheets

SYSTEM AND METHOD FOR REMOTE MONITORING UTILIZING A RECHARGEABLE BATTERY

FIELD OF THE INVENTION

The present invention generally relates to a system and a method for remotely monitoring, and, more specifically, to a system and a method for remotely monitoring a person using a portable unit that is powered by a self-recharging battery.

BACKGROUND INFORMATION

Medical devices that monitor a biological parameter of a patient are often implanted with a battery. Typically, the battery is replaced before the energy supply is substantially drained. A conventional battery implanted in the patient does not generally reveal the amount of remaining energy supply at a given time. Thus, a conventional battery is replaced periodically. This results in a waste of batteries as well as possibly subjecting the patient to invasive surgery which carries with it enhanced costs, labor and risk.

Some medical devices are powered by rechargeable batteries; however, such batteries still require the patient to make hospital visits in which an external power supply device is coupled to the rechargeable battery. This may require an uncomfortable procedure in which the patient is hooked up to electrodes or subjected to high intensity electromagnetic radiation.

What is needed to help avoid these disadvantages is a portable monitoring unit that is powered by a self-recharging battery.

SUMMARY OF THE INVENTION

The present invention provides for a system for remotely monitoring a person, which includes a portable unit with a self-recharging battery, the portable unit being adapted to monitor a biological parameter and a physical position or location of the person; a global positioning satellite transmitting global positioning system (GPS) data to the portable unit; and a central unit disposed remotely from the portable unit, the central unit being in communication with the portable unit via a ground station.

The present invention further provides for a method for remotely monitoring a person including the steps of adapting a portable unit to be powered by a self-recharging battery; self-recharging the self-recharging battery; receiving, from a global positioning system (GPS) satellite to the portable unit, information relating to a physical location; monitoring, at the portable unit, a biological parameter of the person; and wirelessly communicating the information relating to the physical location and the biological parameter of the person from the portable unit to a central unit via a ground station.

The present invention also provides for a self-recharging battery including a photocell disposed proximately to and under a skin surface of a person; a recharging cell coupled to the photocell; and a battery cell coupled to the recharging cell. The photocell is adapted to receive ambient light and is adapted to generate a potential difference across the recharging cell in response to receiving the ambient light. The recharging cell is adapted to store charge in response to the potential difference. The battery cell is adapted to recharge using the stored charge.

The present invention also provides for a self-recharging battery including a transducer disposed in a region of a person with a substantial temperature gradient; a recharging cell coupled to the transducer; and a battery cell coupled to the recharging cell. The transducer is adapted to generate a potential difference across the recharging cell in response to heat flow through the transducer. The recharging cell is adapted to store charge in response to the potential difference. The battery cell is adapted to recharge using the stored charge.

The present invention also provides for a self-recharging battery including a transducer coupled to a pulsing blood vessel; a rectifier coupled to the transducer; a recharging cell coupled to the rectifier; and a battery cell coupled to the recharging cell. The transducer is adapted to generate an alternating electrical signal in response to the pulsing blood vessel. The rectifier is adapted to rectify the alternating electrical signal. The recharging cell is adapted to store charge in response to the rectified electrical signal. The battery cell is adapted to recharge using the stored charge.

The present invention also provides for a self-recharging battery including a transducer coupled to a human voice box of a person; a rectifier coupled to the transducer; a recharging cell coupled to the rectifier; and a battery cell coupled to the recharging cell. The transducer is adapted to generate an alternating electrical signal in response to acoustic waves generated by the human voice box. The rectifier is adapted to rectify the alternating electrical signal. The recharging cell is adapted to store charge in response to the rectified electrical signal. The battery cell is adapted to recharge using the stored charge.

The present invention also provides for a self-recharging battery including a transducer disposed proximately to and under a skin surface of a person; a rectifier coupled to the transducer; a recharging cell coupled to the rectifier; and a battery cell coupled to the recharging cell. The transducer is adapted to generate an alternating electrical signal in response to acoustic waves generated by an ambient environment. The rectifier is adapted to rectify the alternating electrical signal. The recharging cell is adapted to store charge in response to the rectified electrical signal. The battery cell is adapted to recharge using the stored charge.

DETAILED DESCRIPTION

Although the present invention is generally applicable to systems and methods for remote monitoring, the following embodiments according to the present invention contemplate systems and methods for remotely monitoring a person.

Figure 1:
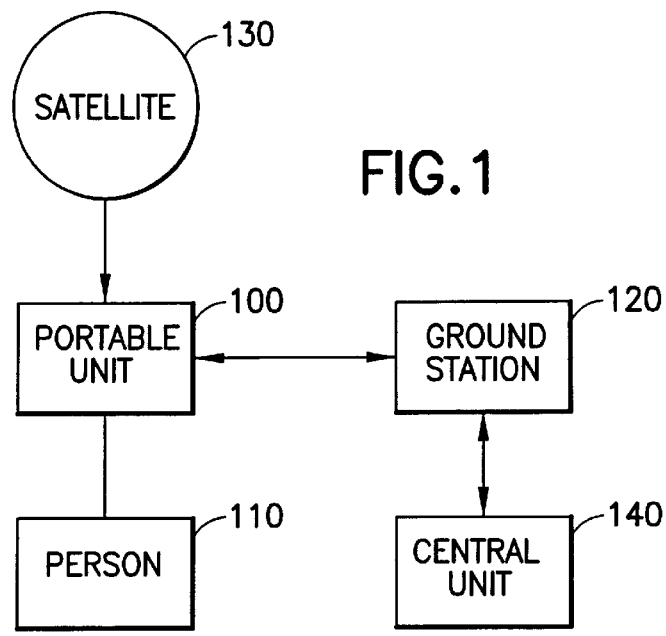
FIG. 1 illustrates an embodiment of a system and a method for remotely monitoring of a person according to the present invention.

FIG. 1 illustrates an embodiment of a system and a method for remotely monitoring a person according to the present invention. A portable unit 100 is coupled to a person 110 that is to be monitored. The portable unit 100 is coupled to a satellite 130. The satellite 130 may be, for example, a set or an array of satellites of an existing global positioning system (GPS). The portable unit 100 is coupled to a ground station 120. The ground station 120 may be, for example, a part of an existing mobile phone grid or a radio communications array. The ground station 120 is coupled to a central unit 140.

The portable unit 100 is adapted to monitor biological parameters of the person 100. The portable unit, may monitor acoustic, thermal, mechanical, chemical, electrical and/or electromagnetic parameters, for example, related to human biological parameters including, for example, temperature, heart rate, blood flow rate, muscular activity, respiratory rate, and brain activity of the person being monitored.

Furthermore, the portable unit 100 is adapted to monitor the physical location of the person 110. In an embodiment according to the present invention, the portable unit 100 receives GPS data transmitted by the satellite 130. With the GPS data, information relating to a physical location of the person 110 may be determined.

In an embodiment according to the present invention, the central unit 140 makes a request for information to the ground station 120, with which the central unit 140 is in two-way communication. The ground station 120 wirelessly transmits an interrogation signal to the portable unit 100, with which the ground station 120 is in two-way wireless communication. In response to the interrogation signal, the portable unit 100 wirelessly transmits information relating to the physical location and/or the human biological parameters of the person 110 being monitored. Further information can be sent that is stored in the portable unit 100 such as, for example, identifying information, personal information or special medical information such as personal medical conditions. The ground station 120 sends information relating to information received from the portable unit 100 to the central unit 140. The information received by the central unit 140 can ultimately be stored, displayed, printed, processed or sent to other central units in a network, for example.

The central unit 140, which may be located in a hospital or a monitoring center, for example, may make the request for information periodically or aperiodically, for example, by manual intervention or a command triggered by a particular circumstance. Furthermore, the central unit 140 may be in wire-to-wire or wireless communication with the ground station 120.

In another embodiment according to the present invention, the portable unit 100, without the receipt of the interrogation signal from the ground station 120, periodically sends information to the ground station 120. Information relating to the received information is sent by the ground station 120 to the central unit 140. In yet another embodiment according to the present invention, the portable unit 100 sends information to the ground station 120 in response to a particular circumstance monitored by the portable unit 100 or in response to a manual command by the person 110 being monitored. For example, the portable unit 100 may send information to the ground station 120 in response to a particular biological parameter which may be indicative of a dangerous medical condition. In another example, the portable unit 100 sends information to the ground station 120 in response to a manual actuation of a switch or a specifically programmed button by the person 110.

The processing of data relating to, for example, the physical location and/or the human biological parameters of the person 110 being monitored may occur either in the portable unit 100, the ground station 120, the central unit 140 or some combination thereof. For example, the portable unit 100 may receive GPS data from the satellite. The GPS data is processed by the portable unit 100, the portable unit 100 calculating the physical location of the person 110 before sending the calculated physical location to the ground station 120 and, subsequently, to the central unit 140.

Alternatively, the GPS data received by the portable unit 100 may be sent to the ground station 120, which processes the information and calculates the physical location of the person 110, the calculated physical location of the person being sent to the central unit. In yet another alternative, the GPS data is sent to the portable unit 100 which sends the information to the ground station 120 which, in turn, sends the information to the central unit 140. In this embodiment, it is the central unit 140 which processes the GPS data and calculates the physical location of the person 110. Furthermore, the present invention contemplates a distributed processing scheme in which part of the processing of the information received by the portable unit 100 from the person 110 and/or the satellite 130 is processed, in part, by a combination of the portable unit 100, the ground station 120 and/or the central unit 140.

Figure 2:
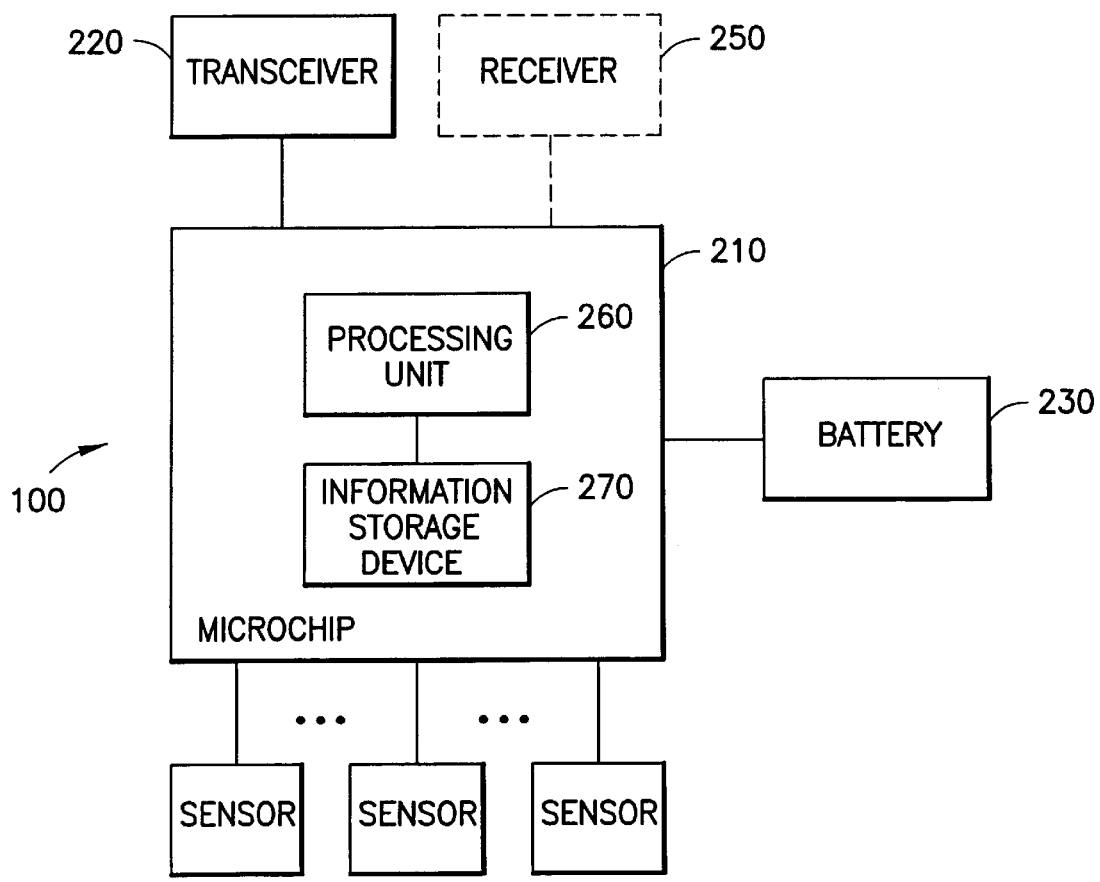
FIG. 2 illustrates an embodiment of a portable unit according to the present invention.

FIG. 2 illustrates an embodiment of a portable unit 100 according to the present invention. The portable unit 100 includes a microchip 210, a transceiver 220, a self-recharging battery 230 and at least one sensor 240. The portable unit 100 may optionally include a receiver 250. Furthermore, the microchip 210 includes a processing unit 260 and an information storage device 270.

Although FIG. 2 illustrates some parts included on the microchip 210 and some parts coupled to the microchip 210, one of ordinary skill in the art understands, and the present invention contemplates, that different levels of integration may be achieved by integrating any of the coupled parts as illustrated in FIG. 2 onto the microchip 210.

The self-recharging battery 230, the at least one sensor 240, the transceiver 220 and, optionally, the receiver 250 are each coupled to the microchip 210. In an embodiment according to the present invention, the at least one sensor 240, the transceiver 220 and, optionally, the receiver 250 are each coupled to the processing unit 260, which, in turn, is coupled to the information storage device. The self-recharging battery 230 powers the microchip 210, including the processing unit 260 and the information storage device 270. The self-recharging battery 230 may also power directly or indirectly the transceiver 220, the at least one sensor 240 and/or, optionally, the receiver 250.

In an embodiment according to the present invention, the transceiver 220 is adapted to be in two-way wireless communication with the ground station 120 and in one-way wireless communication with the satellite 130. The transceiver 220 may be a single antenna or an antenna array, for example.

In another embodiment according to the present invention, the portable unit 100 includes the transceiver 220 and the receiver 250. In this embodiment, the transceiver 220 is in two-way wireless communication with the ground station 120 and the receiver 250 is in one-way wireless communication with the satellite 130. The use of the transceiver 220 and the receiver 250 is advantageous in that the portable unit 100 generally consumes less energy. GPS frequencies tend to be relatively high and sending information over such frequencies by the portable unit 100 via the transceiver 220 can be energy intensive. This embodiment contemplates the receiver 250 being adapted for receiving at high frequencies and the transceiver 220 being adapted for receiving and sending at lower frequencies. The sending of information over lower frequencies by the transceiver 220 results in less energy consumption by the portable unit 100.

The at least one sensor 240 is adapted to monitor acoustic, thermal, mechanical, chemical, electrical and/or electromagnetic parameters, for example, related to human biological parameters including, for example, temperature, heart rate, blood flow rate, muscular activity, respiratory rate, and/or brain activity of the person being monitored. The conversion of acoustic, thermal, mechanical, chemical, electrical and/or electromagnetic parameters into electrical signals, for example, is understood by one of ordinary skill in the art and is not detailed further.

The microchip 210 includes the processing unit 260 and the information storage device 270 in an embodiment according to the present invention. The processing unit 260 may include, for example, a microprocessor, a cache, input terminals and output terminals. The processing unit 260 may include an information storage device which includes an electronic memory which may or may not include the cache of the processing unit 260.

In operation, according to at least one embodiment of the present invention, the receiver 250 receives GPS data from the satellite 130. The GPS data is received by the microchip 210 and, in particular, the processing unit 260. Although the GPS data is continuously received by the receiver 250, the processing unit 260 may periodically or aperiodically (i.e., via manual intervention or as a function of circumstance, for example) receive the GPS data. The GPS data may then be processed in the processing unit 260 which may include determining the physical location of the person 110 being monitored. The GPS data and/or the determined physical location are stored in the information storage device 270.

The at least one sensor 240 senses biological parameters of the person 110. These biological parameters are converted into electrical signals by the at least one sensor 240 and received by the processing unit 260. The sensing of biological parameters by the at least one sensor 240 may be a periodic or an aperiodic function (i.e., triggered by a request from the processing unit 260 or as a function of circumstance, for example). The processing unit 260 may process the electrical signals by converting them into information relating to, for example, a measure of temperature, heart rate, blood flow rate, muscular activity, respiratory rate, and/or brain activity. The processing unit 260 stores the processed and/or unprocessed electrical signals in the information storage device 270. The transceiver 220 receives the interrogation signal, for example, from the ground station 120. The transceiver 220 then sends the interrogation signal to the microchip 210, in particular, to the processing unit 260. Upon receiving the interrogation signal the processing unit 260 uploads the information stored in the information storage device onto the transceiver 220. The transceiver then sends the uploaded information to the ground station 120.

In another embodiment according to the present invention, the microchip is activated only when the transceiver 220 receives the interrogation signal from the ground station 120. This embodiment has an advantage in that energy consumption is minimized. Upon receiving the interrogation signal, the processing unit 260 accepts data from the receiver 250 and the at least one sensor 240. The processing unit 260 may accept the data over a time interval to achieve more precise data or to develop a history of data. Such data may be processed and/or stored in the information storage device 270. Upon completion of the processing and/or storing of the data, the information contained in the information storage device is uploaded onto the transceiver 220 and transmitted to the ground station 120. After completing the transmission of the uploaded data via the transceiver 220, the processing unit 260 is no longer active in receiving, processing and/or storing information until the next interrogation signal is received from the ground station.

In another embodiment according to the present invention, the transceiver 220, without the optional receiver 250, is adapted to receive the GPS data from the satellite 130 and the interrogation signal from the ground station 120. Furthermore, the transceiver 220 transmits information from the processing unit 260 to the ground station. Operation is similar as described above.

The information storage device 270 may also store preset information relating to identification, personal information or special medical information, for example. This information may have been programmed before the coupling of the portable device 100 to the person 110. Alternatively, the information may have been transmitted to the portable device 100 after the portable device 100 was coupled to the person 110. Such information may include the person's name, home address, phone number and/or a listing of relatives to contact in case of emergency. Furthermore, the information permanently stored in the portable device 100 may relate to special medical information such as allergies to medication or that the patient is diabetic or asthmatic, for example. All of this information may be uploaded onto the transceiver 220 and transmitted to the ground station 120. Such information may be of special significance to medical personnel when the person is disoriented or unconscious and unable to communicate.

FIGS. 3–8 illustrate exemplary embodiments of the self-recharging battery 230 according to the present invention. A self-recharging battery 230 is advantageous in a method and a system for remote monitoring.

Figure 3:
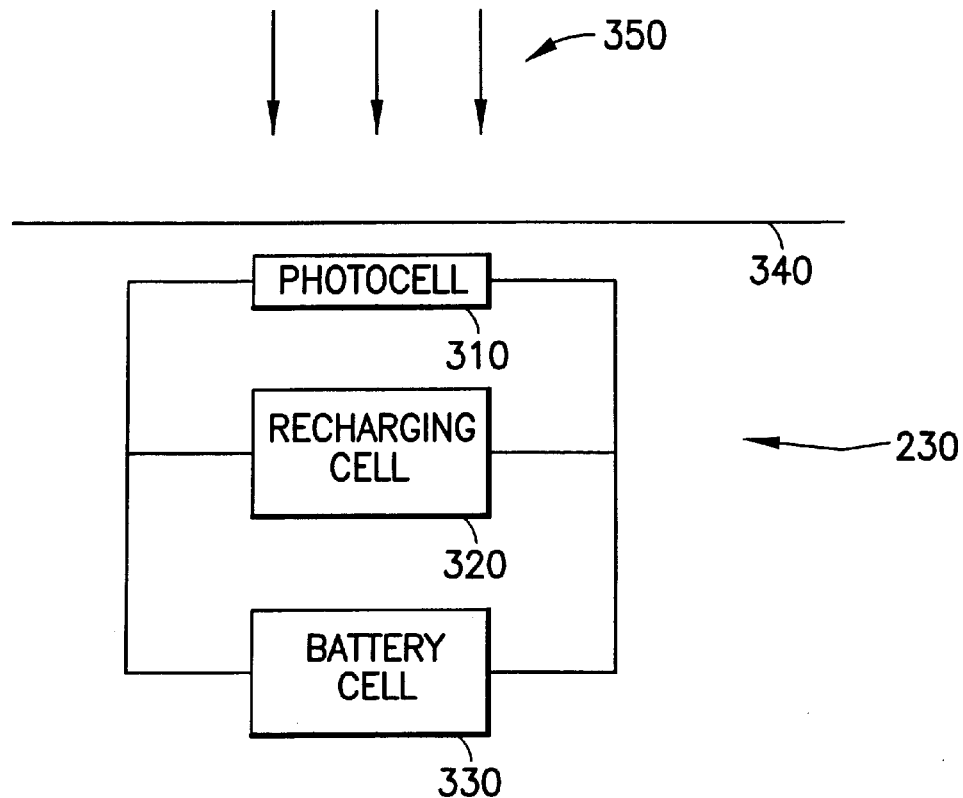
FIG. 3 illustrates an embodiment of a self-recharging battery according to the present invention.

FIG. 3 illustrates an embodiment of the self-recharging battery 230 according to the present invention. The self-recharging battery 230 includes a photocell 310, a recharging cell 320 and a battery cell 330. The photocell 310 is disposed proximately to a skin surface 340 of the person 110. In the illustrated example, the photocell 310 is just under the skin surface 340. The photocell 310 is coupled to the recharging cell 320. In one embodiment, the recharging cell is a capacitor. The recharging cell 320 is coupled to the battery cell 330. The battery cell 330 is coupled to and powers the microchip 210.

In operation, ambient light 350 (e.g., environmental light, natural light) penetrates the skin surface 340. The ambient light 350 is absorbed by the photocell 310. In response to the ambient light 350 being absorbed by the photocell 310, the photocell 310 generates a potential difference (e.g., a voltage) across the recharging cell 320. The recharging cell 320 stores charge which, in turn, is used to recharge the battery cell 330.

Figure 4:
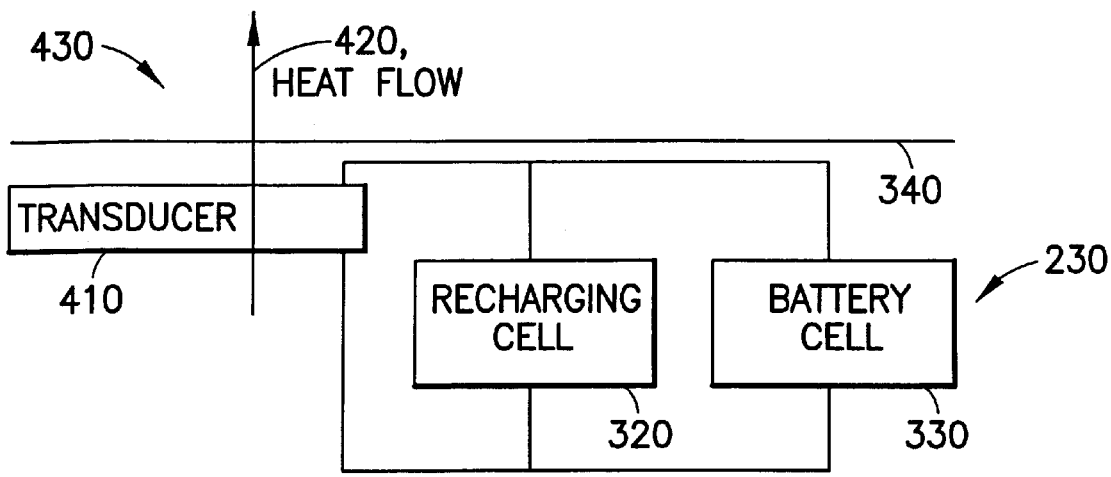
FIG. 4 illustrates another embodiment of the self-recharging battery according to the present invention.

FIG. 4 illustrates another embodiment of the self-recharging battery 230 according to the present invention. The self-recharging battery 230 includes a transducer 410, the recharging cell 320 and the battery cell 330. In the illustrated example, the transducer 410 is disposed proximately to the skin surface 340. Because of differences in temperature between the body just below the skin surface 340 and the ambient atmosphere 430, a heat flow 420 is generated. In part, the heat flow 420 passes through the transducer 410. The transducer 410 may be, for example, a heat sensitive semiconductor transducer. The heat flow 420 passing through the transducer 410 creates a potential difference between opposite sides of the transducer. The potential difference is provided across the recharging cell 320, the recharging cell 320 storing charge. The stored charge is used to recharge the battery cell 330.

Figure 5:
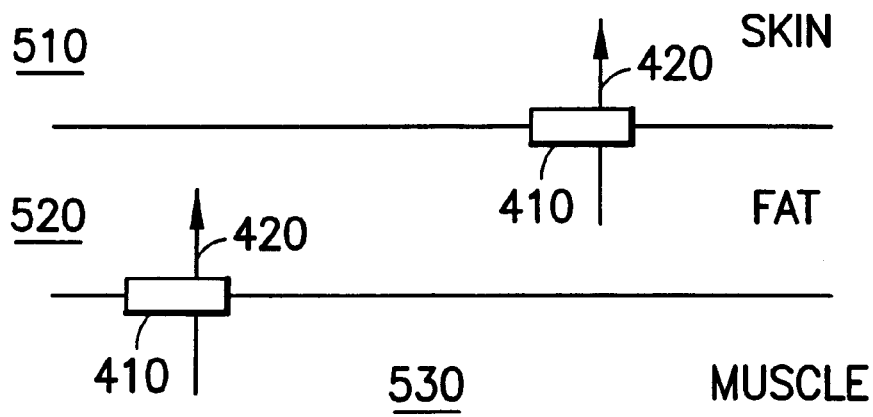
FIG. 5 illustrates two possible locations for a transducer of the self-recharging battery according to the present invention.
Figure 6:
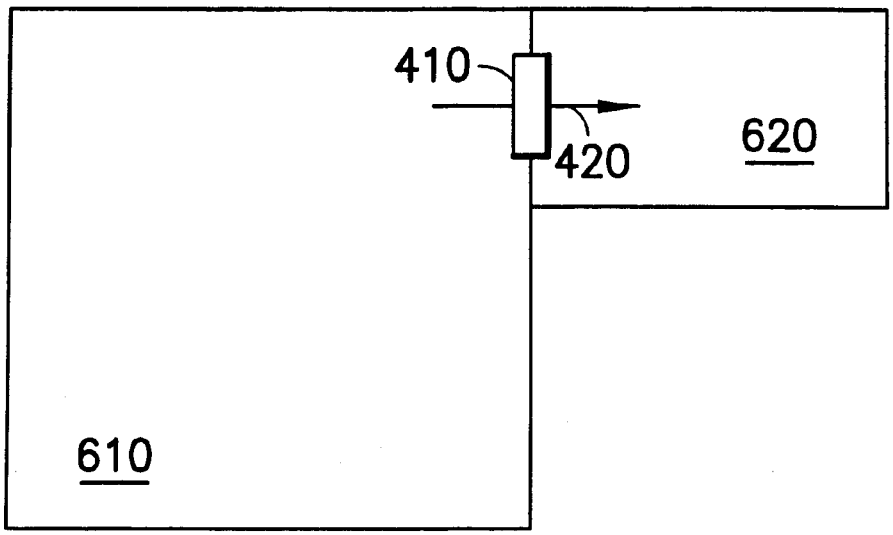
FIG. 6 illustrates another possible location for the transducer of the self-recharging battery according to the present invention.

Although FIG. 4 illustrates a temperature difference between the skin surface 340 and the ambient atmosphere 430, other temperature differences may be employed. For example, FIG. 5 illustrates that the transducer 410 may be placed between a fat layer 520 and a muscle layer 530, or between the fat layer 520 and a skin layer 510. Since each layer 510, 520, 530 has different relative thermal properties, different heat flows can be generated. Accordingly, the effectiveness of the transducer 410 as a recharger is dependent upon the location within the body and upon what materials are employed in creating the heat flow. FIG. 6 illustrates that the transducer 410 may be disposed between a first body part 610 and a second body part 620. The transducer 410 employs the heat flow from the first body part 610 to the second body part 620 in charging the recharging cell 320.

Figure 7:
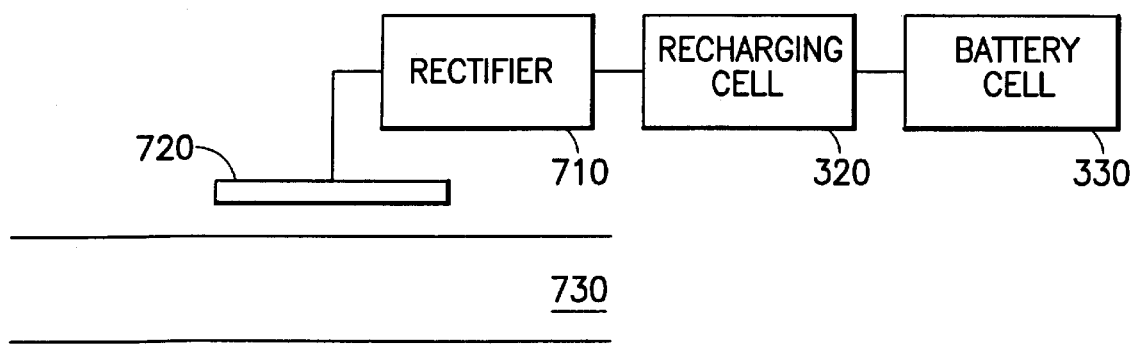
FIG. 7 illustrates still another embodiment of the self-recharging battery according to the present invention.

FIG. 7 illustrates an embodiment of the self-recharging battery 230 according to the present invention. As the schematic indicates, the self-recharging battery 230 includes the battery cell 330, the recharging cell 320, a rectifier 710 and a transducer 720 (e.g., a piezo-electric device). The battery cell 330 is coupled to the recharging cell 320 which, in turn, is coupled to the rectifier 710 which, in turn, is coupled to the transducer 720 which, in turn, is coupled to a blood vessel 730.

In operation, blood is naturally pulsed through the blood vessel 730 causing the blood vessel 730 to have a cycle of expansion and compression. The expansion and compression of the blood vessel 730 is hereinafter referred to as the pulse. The pulse acts upon the transducer 720. The mechanical pressure provided on the transducer 720 by the pulse causes the transducer 720 to generate an alternating electrical signal. The alternating electrical signal passes through the rectifier 710. The recharging cell 320 uses the rectified electrical signal to store charge which, in turn, is used to recharge the battery cell 330.

Figure 8:
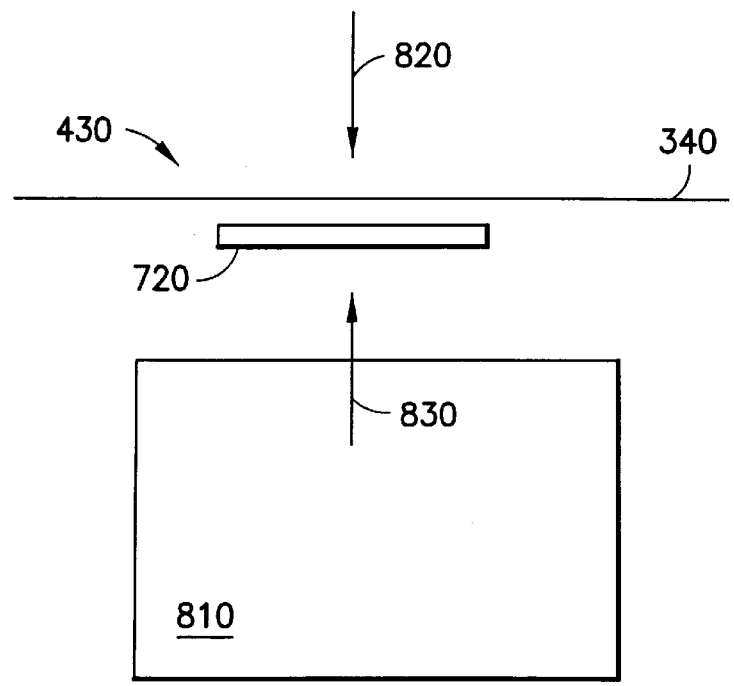
FIG. 8 illustrates a possible location for a transducer of the self-recharging battery according to the present invention.

FIG. 8 illustrates the placement of the transducer 720 in an advantageous location proximate to the skin surface 340 and to a human voice box 810 from which resonates audible sounds (e.g., talking). The transducer 720 (e.g., a microphone) is stimulated either by the vibrations generated by the voice box 810 as indicated via sound waves 830 or by vibrations generated in the ambient atmosphere 430 as indicated by sound waves 820. Thus, via the transducer 720, the self-recharging battery 230 is recharged when the person 110 is talking, for example, or when the person 110 is in a noisy ambient environment.

In the foregoing description, the method and the system of the present invention have been described with reference to specific embodiments. It is to be understood and expected that variations in the principles of the method and the system herein disclosed may be made by one of ordinary skill in the art and it is intended that such modifications, changes and substitutions are to be included within the scope of the present invention as set forth in the appended claims. The specification and the drawings are accordingly to be regarded in an illustrative, rather than in a restrictive sense.

What is claimed is:

1. A system for remotely monitoring a living being, comprising:
    a portable unit including a self-recharging battery, the portable unit being adapted to monitor a biological parameter and a physical location of the living being, the self-recharging battery being rechargeable based on a physiological condition of the living being;
    the portable unit further adapted to receive global positioning system (GPS) data; and
    a central unit disposed remotely from the portable unit, the control unit being in communication with the portable unit, the central unit adapted to receive information indicative of the biological parameter and physical location of the living being from the portable unit.

2. A portable unit for remote monitoring of a living being, the unit comprising:
    a self-recharging battery
    wherein the self-recharging battery includes a photocell, a recharging cell and a battery cell, the photocell being coupled to the recharging cell, the recharging cell being coupled to the battery cell,
    wherein the photocell is disposed proximately to and under a skin surface of the living being,
    wherein the photocell is adapted to receive ambient light and is adapted to generate a potential difference across the recharging cell in response to receiving the ambient light,
    wherein the recharging cell is adapted to store charge in response to the potential difference, and
    wherein the battery cell is adapted to recharge using the stored charge.

3. A portable unit for remote monitoring of a living being, the unit comprising:
    a rechargeable battery,
    wherein the rechargeable battery includes a transducer, a recharging cell and a battery cell, the transducer being coupled to the recharging cell, the recharging cell being coupled to the battery cell,
    wherein the transducer is disposed in a region with a substantial temperature gradient,
    wherein the transducer is adapted to generate a potential difference across the recharging cell in response to heat flow through the transducer,
    wherein the recharging cell is adapted to store charge in response to the potential difference, and
    wherein the rechargeable battery cell is adapted to recharge using the stored charge.

4. A portable unit for remote monitoring of a living being, the unit comprising:
    a rechargeable battery;
    wherein the rechargeable battery includes a transducer, a rectifier, a recharging cell and a battery cell, the transducer being coupled to the rectifier, the rectifier being coupled to the recharging cell, the recharging cell being coupled to the battery cell,
    wherein the transducer is coupled to a pulsing blood vessel,
    wherein the transducer is adapted to generate an alternating electrical signal in response to the pulsing blood vessel, wherein the rectifier is adapted to rectify the alternating electrical signal, wherein the recharging cell is adapted to store charge in response to the rectified electrical signal, and wherein the battery cell is adapted to recharge using the stored charge.

5. A portable unit for remote monitoring comprising:

a rechargeable battery;

wherein the rechargeable battery includes a transducer, a rectifier, a recharging cell and a battery cell, the transducer being coupled to the rectifier, the rectifier being coupled to the recharging cell, the recharging cell being coupled to the battery cell, wherein the transducer is disposed proximately to and under the skin surface of the living being, wherein the transducer is adapted to generate an alternating electrical signal in response to acoustic waves generated by an ambient environment, wherein the rectifier is adapted to rectify the alternating electrical signal, wherein the recharging cell is adapted to store charge in response to the rectified electrical signal, and wherein the stored charge recharges the battery cell.

6. A portable unit for remote monitoring of a living being, the unit comprising:

a rechargeable battery;

wherein the rechargeable battery includes a transducer, a rectifier, a recharging cell and a battery cell, the transducer being coupled to the rectifier, the rectifier being coupled to the recharging cell, the recharging cell being coupled to the battery cell, wherein the transducer is coupled to a human voice box, wherein the transducer is adapted to generate an alternating electrical signal in response to acoustic waves generated by the human voice box, wherein the rectifier is adapted to rectify the alternating electrical signal, wherein the recharging cell is adapted to store charge in response to the rectified electrical signal, and wherein the stored charge recharges the battery cell.

7. A method for remotely monitoring a living being, comprising the steps of:

adapting a portable unit to be powered by a self-recharging battery, the portable unit providing at least one sensor;

self-recharging the self-recharging battery based on a physiological condition of the living being;

receiving, by the portable unit, information relating to a physical location and a biological parameter of the person; and wirelessly communicating the information relating to the physical location and the biological parameter of the person from the portable unit to a central unit via a ground station.

8. A self-recharging battery, comprising:

a photocell disposed proximately to and under a skin surface of a person;

a recharging cell coupled to the photocell; and a battery cell coupled to the recharging cell, wherein the photocell is adapted to receive ambient light and is adapted to generate a potential difference across the recharging cell in response to receiving the ambient light, wherein the recharging cell is adapted to store charge in response to the potential difference, and wherein the battery cell is adapted to recharge using the stored charge.

9. A self-recharging battery, comprising:

a transducer disposed in a region of a living being with a substantial temperature gradient;

a recharging cell coupled to the transducer;

a battery cell coupled to the recharging cell, wherein the transducer is adapted to generate a potential difference across the recharging cell in response to heat flow through the transducer, wherein the recharging cell is adapted to store charge in response to the potential difference, and wherein the battery cell is adapted to recharge using the stored charge.

10. The self-recharging battery according to claim 9, wherein the transducer is disposed proximately to and under the skin surface of the living being, and wherein the substantial temperature gradient is between an ambient environment and a region disposed proximately to and under the skin surface.

11. The self-recharging battery according to claim 9, wherein the transducer is disposed between a skin layer and a fat layer of the living being, and wherein the substantial temperature gradient is between the skin layer and the fat layer.

12. The self-recharging battery according to claim 9, wherein the transducer is disposed between a first body part and a second body part of the living being, and wherein the substantial temperature gradient is between the first body part and the second body part.

13. A self-recharging battery, comprising:

a transducer coupled to a pulsing blood vessel;

a rectifier coupled to the transducer;

a recharging cell coupled to the rectifier; and a battery cell coupled to the recharging cell, wherein the transducer is adapted to generate an alternating electrical signal in response to the pulsing blood vessel, wherein the rectifier is adapted to rectify the alternating electrical signal, wherein the recharging cell is adapted to store charge in response to the rectified electrical signal, and wherein the battery cell is adapted to recharge using the stored charge.

14. A self-recharging battery, comprising:

a transducer coupled to a human voice box of a person;

a rectifier coupled to the transducer;

a recharging cell coupled to the rectifier; and a battery cell coupled to the recharging cell, wherein the transducer is adapted to generate an alternating electrical signal in response to acoustic waves generated by the human voice box, wherein the rectifier is adapted to rectify the alternating electrical signal, wherein the recharging cell is adapted to store charge in response to the rectified electrical signal, and wherein the battery cell is adapted to recharge using the stored charge.

15. A self-recharging battery, comprising:

a transducer disposed proximately to and under a skin surface of a person;

a rectifier coupled to the transducer;

a recharging cell coupled to the rectifier; and a battery cell coupled to the recharging cell, wherein the transducer is adapted to generate an alternating electrical signal in response to acoustic waves generated by an ambient environment, wherein the rectifier is adapted to rectify the alternating electrical signal, wherein the recharging cell is adapted to store charge in response to the rectified electrical signal, and wherein the battery cell is adapted to recharge using the stored charge.

16. The portable unit of claim 2, wherein the portable unit is adapted to:

monitor a physical location of the portable unit;

receive GPS data; and communicate GPS location information indicative of the physical location to a remote control unit.

17. The portable unit of claim 3, wherein the portable unit is adapted to:

monitor a physical location of the portable unit;

receive GPS data; and communicate GPS location information indicative of the physical location to a remote control unit.

18. The portable unit of claim 4, wherein the portable unit is adapted to:

monitor a physical location of the portable unit;

receive GPS data; and communicate GPS location information indicative of the physical location to a remote control unit.

19. The portable unit of claim 5, wherein the portable unit is adapted to:

monitor a physical location of the portable unit;

receive GPS data; and communicate GPS location information indicative of the physical location to a remote control unit.

20. The portable unit of claim 6, wherein the portable unit is adapted to:

monitor a physical location of the portable unit;

receive GPS data; and communicate GPS location information indicative of the physical location to a remote control unit.

21. A method for charging a portable unit receiving power from a rechargeable battery, the portable unit for remote monitoring of a living being, the method comprising:

recharging the rechargeable battery based on a temperature gradient across a transducer.

22. The method of claim 21 wherein the living being is a person.

23. A method for charging a portable unit receiving power from a rechargeable battery, the portable unit for remote monitoring of a living being, the method comprising:

recharging the rechargeable battery based on a pulsing blood vessel in the living being.

24. The method of claim 23 wherein the living being is a person.

25. A method for charging a portable unit receiving power from a rechargeable battery, the portable unit for remote monitoring of a living being, the method comprising:

recharging the rechargeable battery based on acoustic waves, wherein the acoustic waves are generated by vocal chords of the living being.

26. The method of claim 25 wherein the living being is a person.

* * * * *